(12) United States Patent
Daynes et al.

(10) Patent No.: US 7,728,548 B2
(45) Date of Patent: Jun. 1, 2010

(54) DEFIBRILLATOR BATTERY AUTHENTICATION SYSTEM

(75) Inventors: John C. Daynes, Redmond, WA (US); James S. Neumiller, Redmond, WA (US); Kenneth J. Peterson, Bellevue, WA (US); Richard C. Nova, Kirkland, WA (US); Thomas J. McGrath, Everett, WA (US)

(73) Assignee: Physio-Control, Inc., Redmond, WA (US)

( * ) Notice: Subject to any disclaimer, the term of this patent is extended or adjusted under 35 U.S.C. 154(b) by 166 days.

(21) Appl. No.: 12/131,267

(22) Filed: Jun. 2, 2008

(65) Prior Publication Data

US 2009/0295326 A1 Dec. 3, 2009

(51) Int. Cl.
*H02J 7/00* (2006.01)
(52) U.S. Cl. .......................... 320/106; 607/5
(58) Field of Classification Search ................ 320/106, 320/114, 115, 166; 607/5
See application file for complete search history.

(56) References Cited

U.S. PATENT DOCUMENTS

| | | | |
|---|---|---|---|
| 5,321,392 A | 6/1994 | Skakoon et al. | |
| 5,721,482 A | 2/1998 | Benvegar et al. | |
| 5,939,856 A | 8/1999 | Demuro et al. | |
| 6,072,229 A | 6/2000 | Steijer et al. | |
| 6,127,063 A | 10/2000 | Kowalsky et al. | |
| 6,181,102 B1* | 1/2001 | Andrews et al. | 320/106 |
| 6,223,077 B1 | 4/2001 | Schweizer et al. | |
| 6,249,105 B1* | 6/2001 | Andrews et al. | 320/106 |
| 6,291,966 B1 | 9/2001 | Wendelrup et al. | |
| 6,438,415 B1* | 8/2002 | Powers | 607/2 |
| 6,639,381 B2* | 10/2003 | Tamura et al. | 320/103 |
| 6,873,133 B1* | 3/2005 | Kavounas | 320/103 |
| 6,972,542 B2 | 12/2005 | Patino et al. | |
| 7,250,612 B2* | 7/2007 | Pai-Paranjape et al. | 250/461.1 |
| 2006/0178170 A1 | 8/2006 | Chung et al. | |

* cited by examiner

*Primary Examiner*—Edward Tso
*Assistant Examiner*—Ramy Ramadan
(74) *Attorney, Agent, or Firm*—Shumaker & Sieffert, P.A.

(57) ABSTRACT

A method for operating an external medical device such as a defibrillator includes obtaining a data set from a battery pack and examining the data set to determine whether the battery pack is authenticated for use in the external medical device. If the examination does not confirm the authentication, the method includes causing the device to follow a non-authenticated battery pack protocol. The non-authenticated battery pack protocol may include drawing power from the non-authenticated battery pack only if it is the only available source of power for the external medical device. It may include limiting functionality of the external medical device. It may include modifying the battery status information display for the non-authenticated battery pack. A power system for an external medical device may include a power source external to the medical device and including a memory which stores data indicative of an authorized status of the power source and a processor in the medical device configured to analyze the data and to control a function of the medical device based at least in part on the authorization status.

15 Claims, 3 Drawing Sheets

DEFIBRILLATOR BATTERY AUTHENTICATION SYSTEM

TECHNICAL FIELD

The present invention relates generally to battery systems for medical devices. More particularly, the present invention relates to a batter system for an external defibrillator.

BACKGROUND

Defibrillators are medical devices for providing life-saving electrical therapy to persons experiencing an irregular heart beat, such as ventricular fibrillation (VF). A defibrillator provides an electrical stimulus to the heart in an attempt to convert the irregular heart beat to a normal sinus rhythm. An external defibrillator sends electrical pulses to the patient's heart through external electrodes applied to the patient's chest.

To aid in portability, the typical external defibrillator is capable of operating on battery power. Because defibrillators are intended for use in life-threatening medical emergencies, their power source must meet high standards of safety and reliability. A defibrillator designed for use by ambulance crews and in hospitals typically will use battery packs designed specifically for that particular make and model of defibrillator. These battery packs may be rechargeable or non-rechargeable. A combination of rechargeable and non-rechargeable battery packs are used in some defibrillators. Typical external defibrillators have a useful life longer than that of their battery packs. This necessitates the purchase and deployment of several replacement battery packs over the useful life of the defibrillator.

An external defibrillator owner may find several sources from which to purchase after-market battery packs which are configured to fit in the defibrillator. If an after-market battery pack is not manufactured to the appropriate quality standards, device performance may suffer and safety may be compromised. Unfortunately, whether a particular battery pack meets standards and specifications set by the defibrillator manufacturer may not be readily apparent simply by examining the outward appearance of the battery pack.

BRIEF SUMMARY

In an embodiment, a method for operating an external medical device includes the steps of obtaining a data set from a battery pack; examining the data set to determine whether the battery pack is authenticated for use in the external medical device; and if the examination does not confirm the authentication, causing the external medical device to follow a non-authenticated battery pack protocol.

The non-authenticated battery pack protocol may include the step of drawing power from the non-authenticated battery pack only if it is the only available source of power for the external medical device. The non-authenticated battery pack protocol may include the step of notifying a user of the non-authorized status of the battery pack.

The non-authenticated battery pack protocol may include the steps of limiting functionality of the external medical device. The external medical device may be a defibrillator which has the capability of operating in both of a manual mode and an AED mode, and the step of limiting the functionality of the defibrillator may include limiting the functionality to AED mode. The step of limiting the functionality of the defibrillator may include limiting the patient parameter monitoring functionality of the defibrillator. The step of limiting the patient parameter monitoring functionality of the defibrillator may include the step of disabling one or more of capnography, pulse oximetry, non-invasive blood pressure (NIBP) monitoring, end-tidal $CO_2$ ($EtCO_2$) monitoring, electrocardiogam (ECG) monitoring (which may include 12-lead ECG monitoring), invasive blood pressure monitoring, temperature monitoring, or monitoring of CPR performance (for example, as in a CPR feedback or coaching system).

The step of limiting the functionality of the defibrillator may include limiting or disabling an information display or an information storage function.

In an embodiment where the medical device is a defibrillator, the step of limiting the functionality of the defibrillator may include disabling pacing therapy. The step of limiting the functionality of the defibrillator may include disabling synchronized cardioversion therapy. The step of limiting the functionality of the external medical device may include disabling a charging function.

The non-authenticated battery pack protocol may include the step of modifying the battery status information display for the non-authenticated battery pack.

The step of obtaining a data set from a battery pack may include the step of transmitting a query to the battery pack. The step of obtaining a data set from a battery pack may include the step of transmitting a data set from the battery pack upon device power-on. The step of obtaining a data set from a battery pack may include the step of transmitting a data set from the battery pack upon electrical engagement of the battery pack with the external medical device.

In another aspect of this embodiment where the non-authenticated battery pack protocol includes the step of drawing power from the non-authenticated battery pack only if it is the only available source of power for the external medical device. The method may further include the steps of: before drawing power from the non-authenticated battery pack, determining whether an alternative power source is coupled to the medical device and determining whether power is available from the alternative power source.

In another embodiment, a power system for an external medical device includes a power source external to the medical device and including a memory which stores data indicative of an authorized status of the power source, a processor in the medical device configured to analyze the data and to control a function of the medical device based at least in part on the authorization status.

In this system, the function may be a therapy delivery function or a patient monitoring function, or a power source status information display function.

In this system, the therapy delivery function may be a defibrillation shock delivery function.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Aspects of the invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more processors or other control devices. In addition, those skilled in the art will appreciate that the present invention may be practiced in conjunction with any number of medical devices including practical defibrillator systems and that the system described herein is merely one example application. The connecting lines shown in the various figures contained herein are intended to represent example functional relationships and/or physical couplings between the various elements. It should be noted that many alternative or additional functional relationships or physical connections may be present in a practical embodiment.

Figure 1:
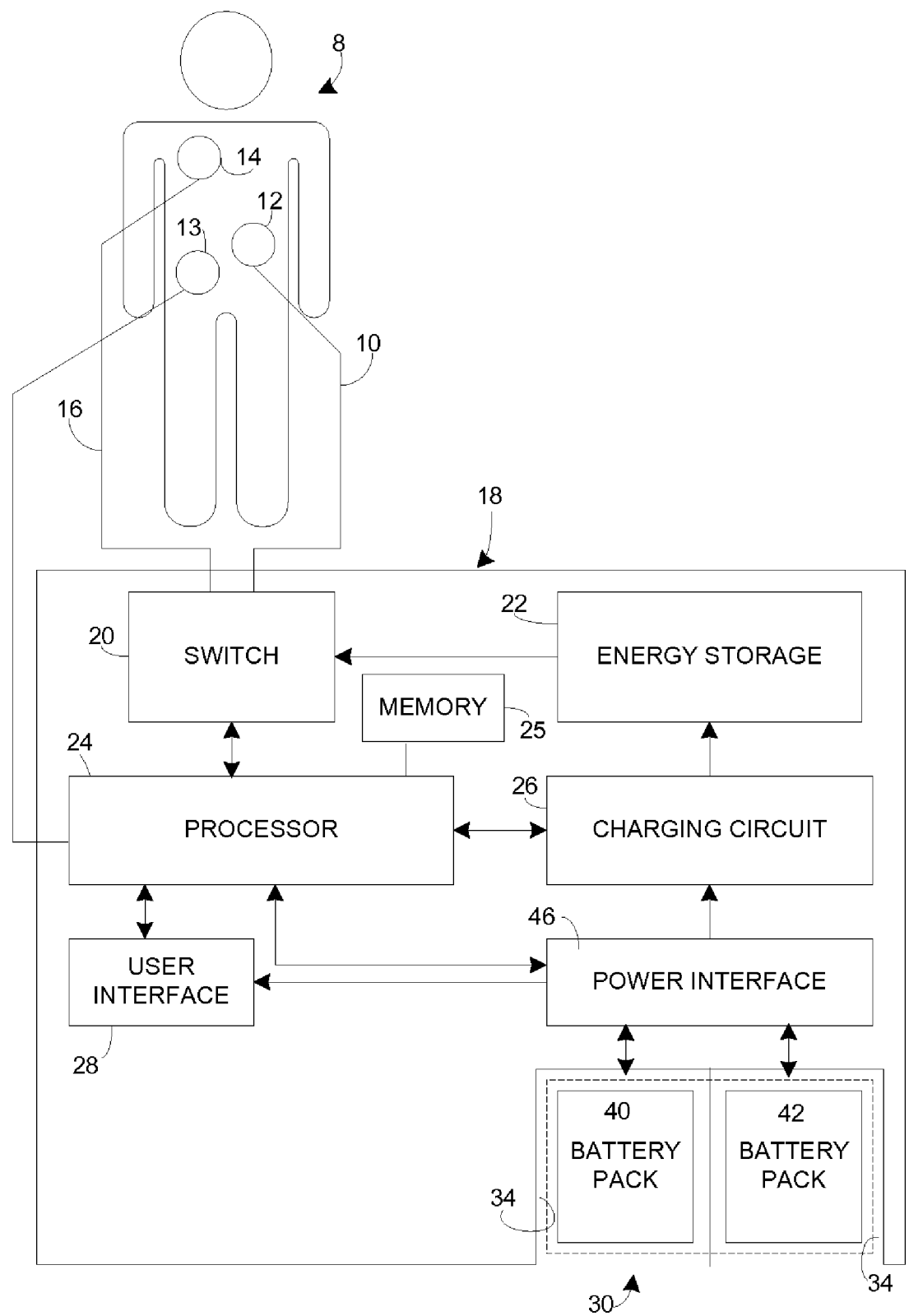
FIG. 1 is a schematic representation of an external defibrillator system configured in accordance with an embodiment of the invention.

FIG. 1 is a block diagram showing a patient 8 coupled to an external defibrillator 18. Defibrillator 18 administers defibrillation therapy to patient 8 via electrodes 12 and 14. The body of patient 8 provides an electrical path between electrodes 12 and 14. Electrodes 12 and 14 are coupled to switch 20 via conductors 10 and 16. Switch 20 couples electrodes 12 and 14 to the output of an energy storage device 22. Switch 20 is of conventional design and may comprise an arrangement of solid-state devices such as silicon-controlled rectifiers or insulated gate bipolar transistors. These may be arranged in an H-bridge configuration.

Energy storage device 22 includes components such one or more capacitors that store the energy to be delivered to patient 8 via electrodes 12, 14. Before a defibrillation pulse may be delivered to patient 8, energy storage device 22 must be charged. A processor 24 analyses the patient's ECG signals that are transmitted from electrodes 12, 14 (or, in some embodiments from separate sensing electrodes, not shown). In a defibrillator 8 operating in an AED mode, the processor determines whether a defibrillating shock is advisable based on the ECG analysis and, if it is, directs a charging circuit 26 to charge energy storage device 22 to a high voltage level. Charging circuit 26 includes, for example, a flyback charger that transfers energy from a power source 30 to energy storage device 22. The processor 24 may be any general purpose processor, microprocessor, controller, or microcontroller that is suitably configured to control the operation of defibrillator. The processor 24 has a memory 25 associated with it. Memory 25 may be any suitable processor-readable medium, including an electronic circuit, a semiconductor memory device, a ROM, a flash memory, or the like. As described in more detail below, memory 25 is capable of storing patient data captured during a resuscitation event, as well as data which can be programmed into the memory 25 during defibrillator manufacturing or during the programming of software updates or upgrades by well-known means.

When the energy stored in energy storage device 22 reaches the desired level, defibrillator 18 is ready to deliver the defibrillation shock. Processor 24 may activate an element of a user interface 28 such as an indicator light, a visual display, or a speaker, that informs the operator that defibrillator 18 is ready to deliver a defibrillation shock to patient 8 or instructs the operator to push a shock button to activate switch 20 and thereby deliver a defibrillation shock to patient 8. In a fully automatic external defibrillator, processor 24 causes the user interface 28 to prompt the operator that defibrillator 18 is ready to deliver a defibrillation shock to patient 8 and to refrain from touching the patient. Processor 24 then activates switch 20 to electrically connect energy storage device 22 to electrodes 12 and 14, and thereby deliver a defibrillation shock to patient 8.

An external defibrillator for use in a hospital or by emergency medical service providers (EMS), commonly called a defibrillator/monitor, may have patient parameter monitoring functionality. Such a defibrillator 8 may include patient parameter sensors 13 such as capnography, pulse oximetry, NIBP, $EtCO_2$, invasive blood pressure, temperature, and other vital sign sensors. Its monitoring functionality may also include patient impedance and ECG (including 12-lead ECG) monitoring. Processor 24 may be configured to analyze sensor data to determine patient condition and to evaluate the efficacy of delivered therapy. Sensor data and results of analyses may be stored in the defibrillator memory 25. The defibrillator 8 may also include sensors for monitoring CPR performance (for example, as a part of a CPR feedback or coaching system). These sensors may include accelerometers, force sensors, impedance sensors or other sensors that detect parameters from which chest compression depth, rate force, or other characteristics of chest compressions may to determined.

The defibrillator 8 may also have cardiac pacing functionality and synchronized cardioversion functionality in addition to its defibrillation therapy functionality. Processor 24 also controls these therapy functions.

A defibrillator 8 such as a defibrillator/monitor may have the capability to function in a manual mode, in which the user chooses one or more parameters of defibrillation therapy delivery such as energy level dosage and timing of delivery, and also in the AED mode described above, where the processor 24 controls therapy delivery parameters. The user interface 28 may include an element which receives an indication of whether the user has chosen manual mode or AED mode, with this choice being communicated to the processor 24. The processor 24 then controls the defibrillator functionality accordingly.

Figure 4:
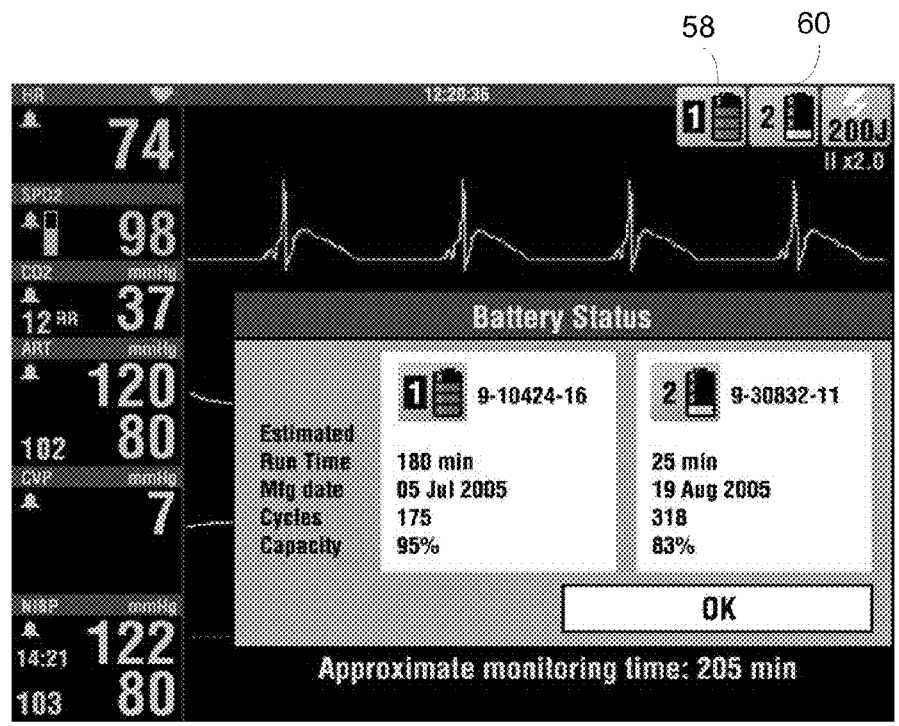
FIG. 4 is an illustration of a first battery status indication displayed on the defibrillator of FIG. 1.

Processor 24 may perform other functions as well, such as controlling the user interface delivery of information concerning the status and operation of the defibrillator and battery pack(s) or other power source engaged with the defibrillator. The user interface may include an LCD screen or other visual display that can display text messages, graphics or pictures that communicate battery pack status, as shown in FIG. 4 for example. The user interface may include an audio interface such as a speaker through which voice prompts or other audio signals indicative of battery status may be communicated. This will be discussed in further detail below.

The power source for the illustrated defibrillator 18 includes a first and second battery pack 40 and 42. Each battery pack 40, 42 is preferably a smart battery capable of self-monitoring and communicating its charge level, maintenance needs and conditions that indicate replacement is needed. An example of a smart battery suitable for use in the defibrillator 18 is discussed in detail in U.S. Pat. No. 6,072,299, which is hereby incorporated by reference herein in its entirety. In the illustrated embodiment, each battery pack 40, 42 is removably engageable with a battery interface in or on the defibrillator housing such as a battery well 34, a compartment, a slot or other battery pack engaging mechanism in or on the defibrillator housing. An example of a battery well interface suitable for use in the illustrated embodiment is discussed in detail in U.S. Pat. No. 6,127,063 which is hereby incorporated by reference herein in its entirety. In another embodiment, a battery pack is internal to the defibrillator. In an embodiment like this, the battery pack may be charged by a method which does not require direct physical contact with a charging device. For example, the battery pack may be charged via a wireless charging method such as inductive charging while the defibrillator is engaged with a docking station. Although a power source including two battery packs is illustrated, it will be understood that the power source can include a single battery pack, or can include more than two battery packs. In another embodiment, the power source can include an AC adapter that is engaged in a battery well and includes a power cable for connection to an AC power source. The AC adapter provides for powering the defibrillator from an AC power source.

When inserted into a battery well 34, a battery pack 40, 42 is electrically coupled to a power interface 46 in the defibrillator which delivers power from one or both of the battery packs 40, 42 to the processor 24, charging circuit 26 and user interface 28. The power interface 46 includes circuitry which can automatically switch from one battery pack to the other, depending on factors such as the relative charge levels of the two battery packs. An example of a power delivery interface and battery switching circuit suitable for use in the illustrated embodiment is discussed in detail in U.S. Pat. No. 6,223,077, which is hereby incorporated by reference in its entirety.

Figure 2:
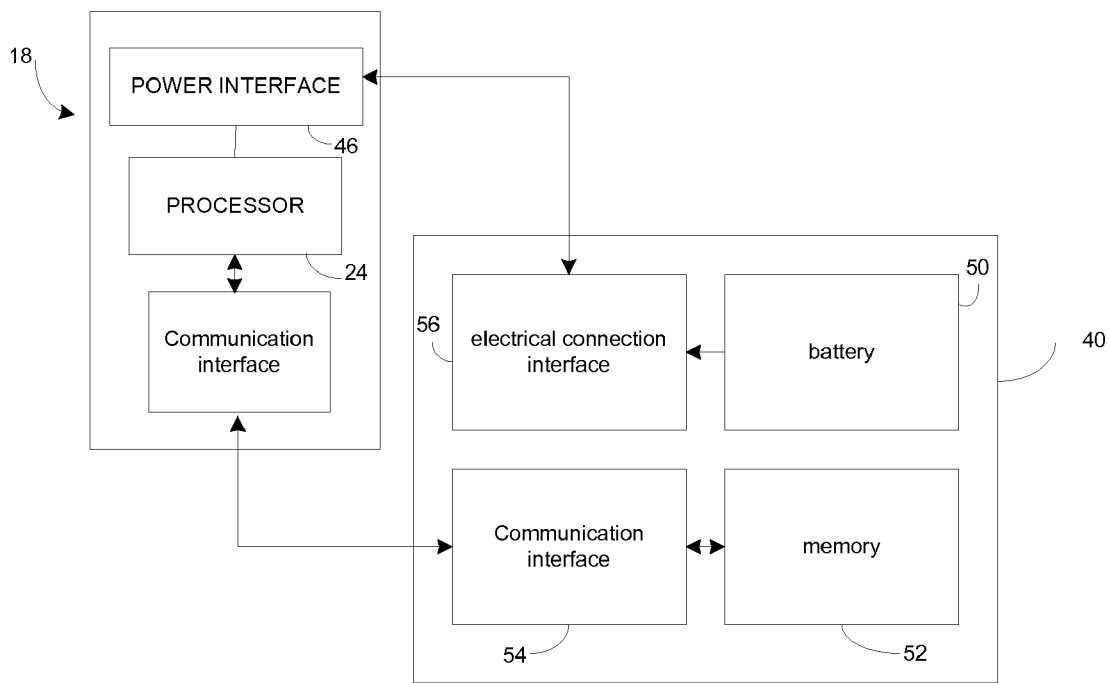
FIG. 2 is a schematic representation of a first example of a battery pack for use in the defibrillator of FIG. 1.

As illustrated in FIG. 2, each battery pack 40, 42 includes one or more batteries 50, a memory 52 and an electrical connection interface 56 which may include one or more electrical connectors that mate with corresponding electrical connectors in the battery well 34 to form an electrical path between the battery 50 and the power interface 46 to transmit power from the battery pack into the defibrillator 18. As used herein, "battery", includes any device that stores electrical energy electrochemically or through any other storage mechanism such as solar cells, flywheels, for example. "Battery" may include, for example, an arrangement of one or more conventional electrochemical cells or fuel cells.

Figure 3:
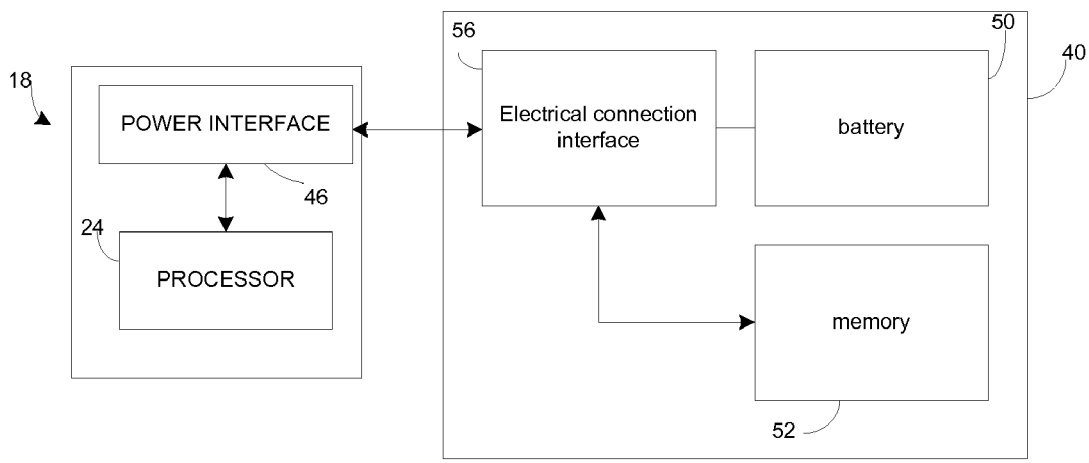
FIG. 3 is a schematic representation of a second example of a battery pack for use in the defibrillator of FIG. 1.

Battery pack 40 of FIG. 2 also includes a communication interface 54 which communicates data from the battery pack memory 52 into the defibrillator 18. The communication interface 54 in FIG. 2 may be a wireless communication interface 54 which communicates with a wireless communication interface in the defibrillator 18. For example, well-known wireless communication techniques in accordance with a standardized data communication protocol such as Bluetooth; IEEE 802.11 (any variation thereof); Ethernet; IEEE 1394 (Firewire); GPRS; USB; IEEE 802.15.4 (Zig-Bee); IrDA (infrared) or induction, may be used to form a communication link between the battery pack 40 and the defibrillator 18. Referring to FIG. 3, the communication interface may be a hard-wired communication interface which forms part of the electrical connection interface 56. In this case, it will communicate data using well-known techniques such as that described in U.S. Pat. No. 6,127,063, which has been discussed above.

The memory 52 in the battery pack 40 stores data which can be used to determine whether the battery pack is authorized by an authenticating party for use with the defibrillator 18. This information will be programmed into the battery pack memory 52, preferably during the manufacturing process. The authenticating party may be the defibrillator manufacturer or a party which the defibrillator manufacturer has authorized and directed to program authentication information into the battery pack memory 52 (for example, an authorized after-market battery pack manufacturer). The authentication information may be a data set which is recognizable by the processor 24 in the defibrillator as a data set that confirms authentication. The data set may be encrypted. It may include a digital key which the defibrillator processor 24 must recognize in order to authenticate the battery pack 40. As additional security measures to safeguard against counterfeiting, the digital key or other authenticating data programmed into battery pack memory 52 may be varied by the authorizing party with corresponding variations in authentication data recognition software that are programmed into defibrillators at various times, for example, during periodic defibrillator software upgrades. For example, battery pack authenticating data can be varied according to year of manufacture, or according to a schedule that corresponds to a defibrillator manufacturer's distribution of software updates for its defibrillators.

In the illustrated embodiment, the processor 24 is configured to cause the defibrillator to query a battery pack 40 which has been placed into the battery well 34 for its authenticating data set. This query may be transmitted to the battery pack via the power interface 46. An authorized battery pack will respond by transmitting the authentication data set. Alternatively, the battery pack may be configured to send its authenticating data set to the defibrillator upon its coupling with the defibrillator, or upon powering on of the defibrillator, with no query from the defibrillator being needed. A processor may be configured to query a battery pack when the defibrillator performs a self-test procedure. In embodiments using a wireless communication link between the battery pack 40 and the defibrillator, the query may be given before the battery pack is engaged with the defibrillator in the battery well. For example, a query may be given when the battery pack comes into proximity of the defibrillator.

In another embodiment, battery pack 40 may include an actuator such as a battery pack status button which provides status information on the battery pack when actuated. With a wireless communication link, authentication information can be transmitted from the battery pack to the defibrillator upon activation of the battery status button.

If data is transmitted from a battery pack to the processor in response to the query (or, in alternative embodiments, upon insertion into the battery well or power-on), the processor will analyze the data to determine if it is authenticating data set. This may be done in any of several ways. For example, the defibrillator processor may verify that the data set includes the authorized digital key. Or, the processor may compare the transmitted data set to one or more data sets stored in defibrillator memory 25 to see if the transmitted data set matches one stored in the defibrillator memory.

It may be advantageous for an authorizing party to program more than one set of identifying data into each defibrillator, so that one of several different corresponding authentication data sets may be used in an authorized battery pack. This may be advantageous to allow pre-planned changes in programmed authorization data sets (for example, data set A programmed into battery packs in manufacturing year X; data set B in manufacturing year Y, etc.), or if several different battery manufacturers will be authorized, to provide a different authorization data set for each authorized battery pack manufacturer.

The identifying data may be programmed into the defibrillator at the time of defibrillator manufacture. Programming of identifying data may be updated from time to time. Software in a defibrillator is sometimes modified or replaced in order to upgrade or update performance of the defibrillator. A modification or replacement of previously programmed identifying data may be made as a part of a software upgrade, or the reprogramming of identifying data may be made independently of any other defibrillator software upgrade.

If an authenticating data set is not transmitted to the defibrillator in response to a query, then the processor may cause the defibrillator to operate under a non-authorized battery pack protocol. A non-authorized battery pack protocol may include one or more of: a reduced or modified functionality of the defibrillator, a modification of information provided to the user concerning the battery pack, and for a defibrillator which uses more than one battery pack, a modified protocol for drawing power from the battery packs.

If the pack is not identified as being authorized, the defibrillator's system functionality may be limited. For example, a defibrillator which has manual operation capability may be restricted to operation in AED mode only or pacing therapy could be disabled. Sensing or monitoring capabilities may be limited. For example, monitoring of one or more of capnography, pulse oximetry NIBP, $EtCO_2$, ECG (e.g., 12-lead ECG), invasive blood pressure or temperature, could be disabled under a non-authenticated battery pack protocol. Monitoring of CPR performance characteristics or CPR coaching, feedback or prompting functions based on that monitoring could be disabled or limited under a non-authenticated battery pack protocol.

If the defibrillator has charging capability, i.e., if a battery pack engaged with the defibrillator could ordinarily be charged from either AC power connected to the defibrillator or from another battery pack engaged with the defibrillator, charging of a battery pack which is not authenticated can be limited or prevented altogether. For example, the level of charge capacity to which the defibrillator will charge a non-authenticated battery pack can be subject to a pre-set limit which is less than full charge capacity. The number of charge cycles which a defibrillator will perform on any non-authenticated battery pack can be limited in number. As another example, a defibrillator could use an unauthenticated battery pack only for charging of authenticated battery packs.

The step of limiting functionality of the defibrillator may include the step of disabling a post-processing function performed on one or more monitored parameters such as those mentioned above. For example, acute myocardial infarction (AMI) detection or alarms, or determination of heart rate or respiration rate, and/or alarms based on a heart rate or respiration rate could be disabled or limited.

The step of limiting functionality of the defibrillator may include the step of limiting or disabling an information storage, transfer or display functionality of the defibrillator. This may include disabling a printer built into the defibrillator, or limiting data transfer out of the defibrillator to a separate printer. Other examples include limiting the information displayed on a user interface display screen and/or limiting the information stored in the defibrillator's memory. For example, a defibrillator may be configured to display only ECG waveforms and no others, to display only a limited set of patient parameters and omit display of others, or to display detected parameters on the defibrillator display screen but not in a printed report. Other alternatives include storing a limited set of patient parameter data (i.e., limited to only certain parameters) or limit the storage time of patent parameter data.

Figure 5:
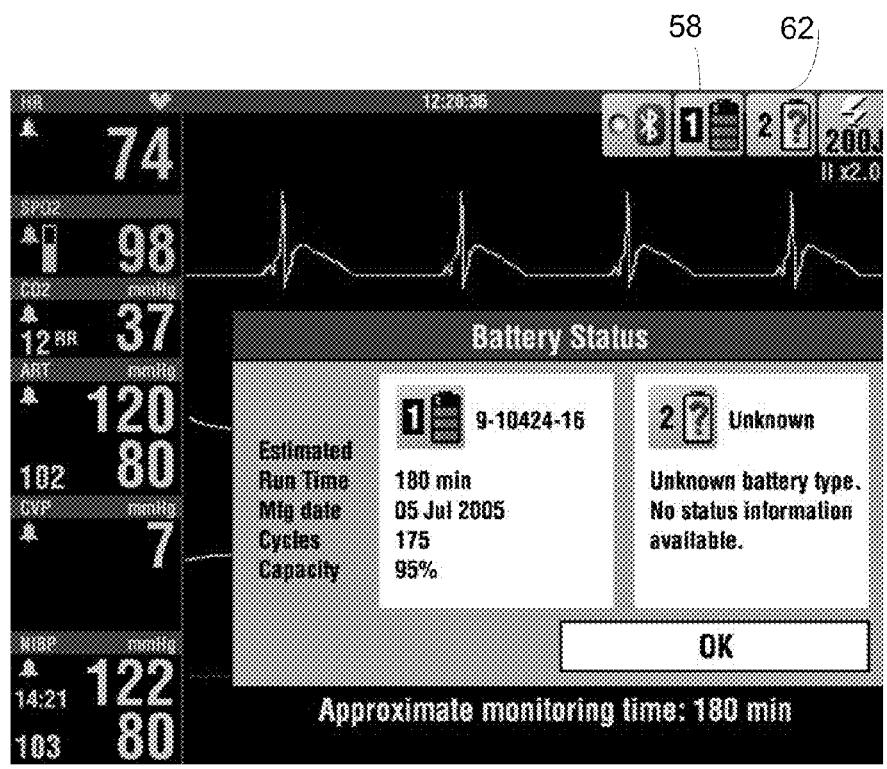
FIG. 5 is an illustration of a second battery status indication displayed on the defibrillator of FIG. 1.

If the battery pack is not identified as being authenticated, a non-authorized battery pack notification protocol may be followed FIG. 4 illustrates an example of a screen display where both battery packs have been confirmed as authenticated. In the illustration, battery charge levels for each battery pack are represented by charge level icons 58, 60, and estimated run times, manufacture date, number of charge/discharge cycles that the battery pack has undergone and absolute capacity for each is displayed in text. In a non-authenticated power source protocol, the processor would cause the screen to display more limited or different information for a non-authenticated battery pack. This information may include, for example, a recommendation for replacement of the unauthenticated battery pack or a warning against its use. FIG. 5 illustrates an example of a graphical display where, instead of displaying battery charge level for non-authenticated battery pack, only a question mark is displayed. Alternatively, a text message such as "Unauthorized battery pack in battery well 2" may be displayed instead of a charge level indication, or in addition to a charge level indication. Another alternative for communication of information concerning an unauthenticated battery pack could include an audio alert, such as a tone or a voice prompt delivering information such as "Unauthorized battery pack in battery well 2". An audio alert could be combined with a visual indicator such as a flashing icon. Where the non-authenticated battery pack protocol also includes modifications to defibrillator functionality, text describing these functionality modifications due to insertion of the non-authenticated battery pack may be displayed on the screen.

In another alternative, the presence of an unauthorized battery pack with the defibrillator can be recorded in a code summary in which information concerning usage of the defibrillator is recorded. It can alternatively or additionally be recorded in the defibrillator's device status log or self-test activity log so that personnel who review the device's status information and self-test results are aware that an unauthenticated battery pack had been in the device.

In embodiments where the defibrillator has the capability to communicate with a remote unit (for example, a remote device management system) the defibrillator can communicate battery authentication information to the remote unit. If the defibrillator is adapted for two-way communication, the remote unit may, upon receiving a notification of an unauthenticated battery, send to the defibrillator a communication including an instruction for the processor to cause a particular action to occur. This may be an instruction to shut down the defibrillator or to modify the processes performed by the defibrillator in some way. The instruction may be provided according to an algorithm performed by a processor at the remote unit (for example, to perform according to one or more of the protocols discussed elsewhere). Alternatively, the instruction to be sent back to the defibrillator may be determined by personnel monitoring battery authentication information at the remote unit.

If the battery pack is not identified as being authenticated, a non-authorized battery pack utilization protocol may be followed. For example, when the processor does not receive an authentication data set from a battery pack, it can cause the defibrillator to operate as if the non-authenticated battery were not present in the device, i.e., to draw power from only the authenticated battery pack. The processor may allow use of an unauthenticated battery pack only if an authenticated battery pack is also available for use by the defibrillator. The processor may allow only a limited number of uses of the unauthenticated battery pack, or may limit the time duration of use of an unauthenticated battery pack. The time duration for use of an unauthenticated battery pack could be limited to a time chosen to accommodate a typical patient usage of the defibrillator, for example, 20 minutes, to avoid an interruption of therapy and monitoring. The processor may allow only a predetermined amount of charge to be drawn from an unauthenticated battery pack. For example, the quantity could be a predetermined charge quantity or could be a predetermined percentage of total available charge in the unauthenticated battery pack.

Alternatively, the processor may cause the power interface to operate in a modified manner. In the illustrated embodiment, the defibrillator 18 has two battery wells, Well 1 and Well 2. If both battery packs are authenticated, the defibrillator will, by default, first draw power from a battery well designated as Well 1. When the battery pack in Well 1 is depleted to a predetermined level, power interface will then switch to the battery pack in Well 2. In a non-authorized battery pack utilization protocol where one battery pack is not confirmed to be authenticated, the power interface 46 may be configured to first draw power from the authenticated battery pack, regardless of whether it is in Well 1 or Well 2. It may be configured to draw power from an unauthenticated battery pack only if no other source of power is available, or only if an authenticated battery is in the other battery well, or not at all. In another alternative, the processor can instruct the defibrillator to fully or partially discharge an unauthenticated battery pack which is engaged in a battery well.

While two levels of functionality (one for an authenticated battery pack and another for a non-authenticated battery pack) have been discussed in connection with the illustrated embodiment, a system could have several functionality levels or several battery use protocols which are invoked based on several authentication status levels. A functionality level or protocol may be chosen based on authentication status level, or upon other battery pack information transmitted from the battery pack to the defibrillator. For example, authenticated battery packs from certain manufacturers, manufacturing facilities, manufacturing lots or dates of manufacture, may be given a first authentication status (e.g., "level 1"), while those of others may be given a second authentication status (e.g., "level 2"), which correspond to a first and a second functionality level or protocol. For example, a first authentication level may correspond to a protocol or functionality level that include features (such as a visual message) which draw a user's attention to battery pack status, while a second authentication level may include modifications to defibrillator functionality which would encourage prompt battery pack replacement (such as a repeated audible prompt). The particular protocol or functionality level may be chosen based on the manufacturer/manufacturing facility, lot identification, manufacturing date or other factors.

This may be useful, for example, to draw a user's attention to a battery pack that is nearing its expiration date by providing a protocol that includes prompts or displays that draw attention to this and which may include defibrillator functionality modifications that encourage prompt battery pack replacement. As another example, where a defibrillator manufacturer has become aware of an issue in a particular manufacturing lot or in battery packs manufactured at a particular facility or in a particular data range which makes their replacement desirable or necessary, defibrillators already in the field may be reprogrammed so that the reprogrammed defibrillators will recognize battery packs which transmit information indicative of being in the affected lot, or form the particular facility or date range, as being non-authenticated or as having an authentication status at a level which results in a modified protocol or functionality level as discussed above.

Although the battery pack authentication system has been described in connection with an external defibrillator for purposes of illustration, it will be understood that the system can be adapted for use with other medical devices also, and for battery chargers used to charge batteries for defibrillators and other medical devices.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A medical device that is capable of operating to defibrillate a patient according to a first protocol if a preset battery authentication is confirmed, and capable of operating to defibrillate the patient according to a second protocol different from the first protocol if the authentication is not confirmed, comprising:

a capacitor for storing an electrical charge that is to be delivered to the patient as part of defibrillating according to either the first protocol or the second protocol regardless of whether the authentication is confirmed;

a battery well for receiving a battery pack therein;

means for receiving a data set from the battery pack when the battery pack is in the battery well; and a processor capable of recognizing whether the received data set confirms the authentication or not, in which according to the first protocol, power is drawn from the battery pack even if the battery pack is not the only available source of power for the device, but according to the second protocol, power is drawn from the battery pack only if the battery pack is the only available source of power for the device.

2. The medical device of claim 1, in which a query is transmitted to the battery pack, and the data set is received responsive to the query.

3. The medical device of claim 1, in which the data set is received responsive to power-on of the device.

4. The medical device of claim 1, in which the data set is received responsive to electrical engagement of the battery pack with the medical device as the battery pack is received in the well.

5. The medical device of claim 1, in which the received data set is encrypted.

6. The medical device of claim 1, in which according to the second protocol, it is further determined whether a power source alternative to the battery pack is coupled to the medical device.

7. The medical device of claim 1, in which according to the first protocol, a first type of indication about a status of the battery pack is displayed at a screen of the device, while according to the second protocol, a second type of indication different from the first type is displayed at the screen.

8. The medical device of claim 1, in which
while a functionality of defibrillating is operable according to both the first protocol and to the second protocol,
a certain functionality other than the functionality of defibrillating is operable according to the first protocol, but not according to the second protocol.

9. The medical device of claim 8, in which
the certain functionality is to monitor a parameter of the patient.

10. The medical device of claim 9, in which
the parameter includes one of capnography, pulse oximetry, non-invasive blood pressure, end tidal $CO_2$, ECG, invasive blood pressure, temperature, and CPR performance monitoring.

11. The medical device of claim 8, in which
the certain functionality is an information display functionality.

12. The medical device of claim 8, in which
the certain functionality is a synchronized cardioversion therapy.

13. The medical device of claim 8, in which
the certain functionality is a pacing therapy.

14. The medical device of claim 1, in which
the medical device exhibits a warning about the authentication not being confirmed when operating according to the second protocol, but not when operating according to the first protocol.

15. The medical device of claim 1, in which
according to the first protocol, the device has the capability of operating in both of a manual mode and an AED mode, but
according to the second protocol, the device has the capability of operating in the AED mode but not the manual mode.

* * * * *

UNITED STATES PATENT AND TRADEMARK OFFICE
CERTIFICATE OF CORRECTION

| | | |
|---|---|---|
| PATENT NO. | : 7,728,548 B2 | Page 1 of 1 |
| APPLICATION NO. | : 12/131267 | |
| DATED | : June 1, 2010 | |
| INVENTOR(S) | : John C. Daynes | |

It is certified that error appears in the above-identified patent and that said Letters Patent is hereby corrected as shown below:

Column 1, line 3, "the present invention relates to a batter system for an external" should read -- the present invention relates to a battery system for an external --

Column 4, line 31, "or other characteristics of chest compressions may to determined" should read -- or other characteristics of chest compressions may be determined --

Column 9, line 61, "which transmit information indicative of being in the affected lot, or form the particular" should read -- which transmit information indicative of being in the affected lot, or from the particular --

Signed and Sealed this
Nineteenth Day of July, 2011

David J. Kappos
*Director of the United States Patent and Trademark Office*